United States Patent [19]

Gaudette et al.

[11] 4,069,249
[45] Jan. 17, 1978

[54] N,N-DI-(HYDROXYBENZYL)-TRIMETHYLENE DIAMINEDIACETIC ACIDS

[75] Inventors: Roger Robert Gaudette, Hudson, N.H.; John Leonard Ohlson, Bedford; Patricia Marie Scanlon, Arlington, both of Mass.

[73] Assignee: W. R. Grace & Co., New York, N.Y.

[21] Appl. No.: 630,792

[22] Filed: Nov. 11, 1975

[51] Int. Cl.² ............... C07C 101/447; C07C 143/67
[52] U.S. Cl. ......................... 260/519; 71/1;
260/429J; 260/429.9; 260/435 R; 260/438.1;
260/438.5 R; 260/439 R; 260/465 D; 260/465
E; 260/501.11; 260/501.12; 260/507 R
[58] Field of Search ............... 260/519, 501.11, 507 R

[56] References Cited

U.S. PATENT DOCUMENTS

| Re. 23,904 | 12/1954 | Bersworth | 260/519 X |
|---|---|---|---|
| 2,824,128 | 2/1958 | Dexter | 260/519 |
| 2,967,196 | 1/1961 | Kroll et al. | 260/519 |
| 3,005,848 | 10/1961 | Knell et al. | 260/519 |
| 3,632,637 | 1/1972 | Martell | 260/519 |
| 3,780,099 | 12/1973 | Scanlon et al. | 260/534 E |

*Primary Examiner*—Dolph H. Torrence
*Attorney, Agent, or Firm*—Elton Fisher

[57] ABSTRACT

A novel chelating agent having the formula

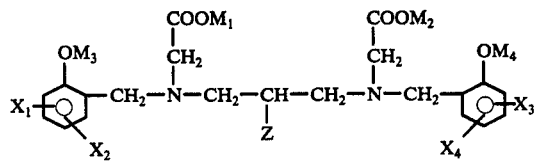

in which
a. each of $X_1$, $X_2$, $X_3$, and $X_4$ is a member selected from the group consisting of (i) hydrogen; (ii) an alkyl group having 1-4 carbon atoms; (iii) —CN; (iv) —SO$_3$M$_1$; (v) —COOM$_1$; (vi) —OM$_3$; (vii) —NO$_2$; (viii) —OH; and (ix)

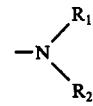

in which each of $R_1$ and $R_2$ is an alkyl group having 1-4 carbon atoms;

b. each of $M_1$, $M_2$, $M_3$, and $M_4$ is a member selected from the group consisting of (i) a hydrogen ion; (ii) an alkali metal ion; (iii) one-half an alkaline earth metal ion; and (vi) an ammonium ion having the formula

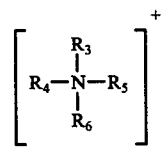

in which each of $R_3$, $R_4$, $R_5$, and $R_6$ is a member selected from the group consisting of (A) hydrogen; (B) an alkyl group having 1-4 carbon atoms; and (C) a hydroxyalkyl group having 1-4 carbon atoms; and c. Z is a member selected from the group consisting of (i) hydrogen; and (ii) hydroxyl.

8 Claims, No Drawings

N,N-DI-(HYDROXYBENZYL)-TRIMETHYLENE DIAMINEDIACETIC ACIDS

BACKGROUND OF THE INVENTION

This invention is in the field of chelating compounds and chelates of said compounds with metallic ions including iron ions, copper ions, cobalt ions, manganese ions, chromium ions, nickel ions, zinc ions, cadmium ions, molybdenum ions, lead ions, and the like.

More particularly this invention is in the field of: (I) a chelating agent (chelating compound) having the formula

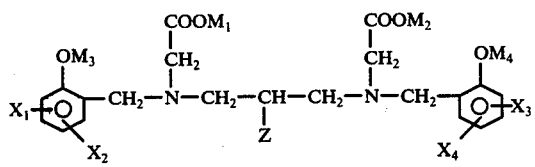

in which $R_1$ through $R_6$, $M_1$ through $M_4$, Z, and $X_1$ through $X_4$ are defined in the Summary of this invention, infra; and (II) chelates of said chelating agent with metallic ions including iron(III) and iron(II) ions.

The following U.S. Patents teach chelating compounds and chelates which are of interest:

| U.S. Pat. No. | Class | Inventor(s) |
|---|---|---|
| Re. 23,904* | 260/518 | Bersworth |
| 2,624,757 | 260/518 | Bersworth |
| 2,624,760 | 260/519 | Bersworth |
| 2,824,128 | 260/519 | Dexter |
| 2,967,196 | 260/507 | Kroll et al |
| 3,038,793 | 71/1 | Kroll et al |
| 3,110,679 | 252/152 | Rubin |
| 3,632,637 | 260/519 | Martell |
| 3,742,002 | 260/439R | Ohlson et al |
| 3,758,540 | 260/439R | Martell |
| 3,780,099 | 260/534E | Scanlon et al |
| 3,780,100 | 260/534E | Scanlon et al |

*Re. 23,904 is a reissue of U.S. Pat. No. 2,624,757

SUMMARY OF THE INVENTION

In summary, this invention is directed to a compound (a chelating agent) having the formula

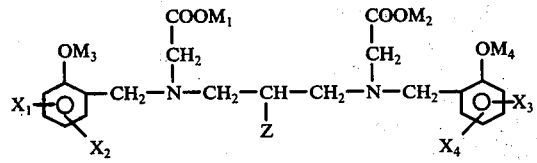

in which
a. each of $X_1$, $X_2$, $X_3$, and $X_4$ is a member selected from the group consisting of (i) hydrogen; (ii) an alkyl group having 1-4 carbon atoms; (iii) —CN; (iv) —$SO_3M_1$; (v) —$COOM_1$; (vi) —$OM_3$; (vii) —$NO_2$; (viii) —OH; and (ix)

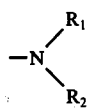

in which each of $R_1$ and $R_2$ is an alkyl group having 1-4 carbon atoms;
b. each of $M_1$, $M_2$, $M_3$, and $M_4$ is a member selected from the group consisting of (i) hydrogen ion; (ii) an alkali metal ion; (iii) ½ an alkaline earth metal ion; and (vi) an ammonium ion having the formula

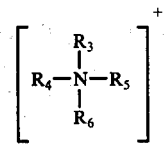

in which each of $R_3$, $R_4$, $R_5$, and $R_6$ is a member selected from the group consisting of (A) hydrogen; (B) an alkyl group having 1-4 carbon atoms; and (C) a hydroxyalkyl group having 1-4 carbon atoms; and
c. Z is a member selected from the group consisting of (i) hydrogen; and (ii) hydroxyl. This invention is also directed to a metal (e.g., iron(III) or iron(II)) chelate of the above-described chelating agent.

The compound of this Summary in which: (a) each of $X_1$, $X_2$, $X_3$, and $X_4$ is hydrogen; (b) each of $M_1$, $M_2$, $M_3$, and $M_4$ is hydrogen or sodium; and (c) Z is hydrogen or hydroxyl is also especially useful; said compound can be designated "Compound S-1".

DESCRIPTION OF PREFERRED EMBODIMENTS

In preferred embodiments this invention is directed to an iron chelate of the compound (chelating agent) of the above Summary. Said iron chelate can be an iron(III) chelate or an iron(II) chelate of said chelating agent.

In another preferred embodiment ("Embodiment A") this invention is directed to a compound (a chelating agent) having the formula

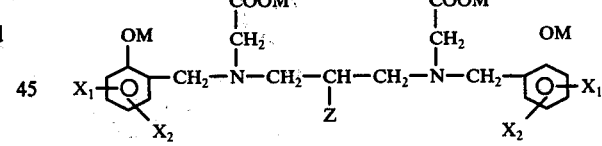

in which
a. each of $X_1$ and $X_2$ is a member selected from the group consisting of (i) hydrogen; (ii) an alkyl group having 1-4 carbon atoms; (iii) —CN; (iv) —$SO_3M_1$; (v) —$COOM_1$; (vi) —$OM_3$; (vii) —$NO_2$; (viii) —OH; and (ix)

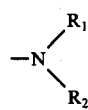

in which each of $R_1$ and $R_2$ is an alkyl group having 1-4 carbon atoms;
b. M is a member selected from the group consisting of (i) hydrogen; (ii) an alkali metal ion; (iii) ½ an alkaline earth metal ion; and (vi) an ammonium ion having the formula

in which each of $R_3$, $R_4$, $R_5$, and $R_6$ is a member selected from the group consisting of (A) hydrogen; (B) an alkyl group having 1–4 carbon atoms; and (C) a hydroxyalkyl group having 1–4 carbon atoms; and c. Z is a member selected from the group consisting of (i) hydrogen; and (ii) hydroxyl.

This invention is also directed to a metal chelate (e.g., iron(III) or iron(II) of the chelating agent of Embodiment A.

This invention is also directed to the compound of Embodiment A in which:
a. M is a hydrogen ion;
b. Z is hydrogen;
c. each of $X_1$ and $X_2$ is hydrogen.

This invention is also directed to a metal (e.g., iron(III) or iron(II)) chelate of the compound of Embodiment A in which:
a. M is a hydrogen ion;
b. Z is hydrogen;
c. each of $X_1$ and $X_2$ is hydrogen.

This invention is also directed to the compound of Embodiment A in which:
a. M is hydrogen;
b. Z is —OH;
c. each of $X_1$ and $X_2$ is hydrogen.

This invention is also directed to a metal (e.g., iron(III) or iron(II)) chelate of the compound of Embodiment A in which:
a. M is hydrogen;
b. Z is —OH;
c. each of $X_1$ and $X_2$ is hydrogen.

In another preferred embodiment ("Embodiment B") this invention is directed to a process for preparing a first acid (a chelating agent) having the formula

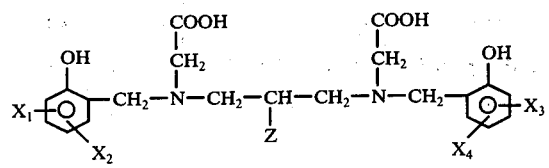

in which Z is H or OH, said process comprising forming a resulting mixture by admixing in an inert reaction medium selected from a first group consisting of: (i) water; (ii) an alcohol selected from a second group consisting of methyl alcohol, ethyl alcohol, isopropyl alcohol, and normal propyl alcohol; (iii) an admixture of water and a member selected from the second group; (iv) acetic acid; and (v) an admixture of water and acetic acid:

a. at least one phenol having the formula

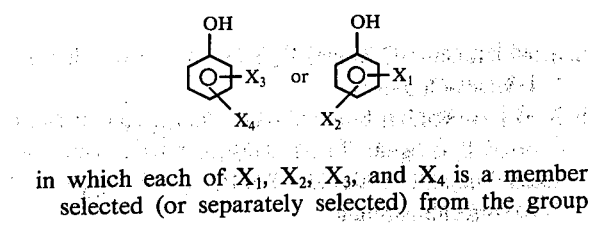

in which each of $X_1$, $X_2$, $X_3$, and $X_4$ is a member selected (or separately selected) from the group consisting of (i) hydrogen; (ii) an alkyl group having 1–3 carbon atoms; (iii) —CN; (iv) —$SO_3M$; (v) —$SO_3H$; (vi) —COOH; (vii) —OH; (viii) —$NO_2$; and (ix)

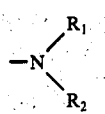

in which each of $R_1$ and $R_2$ is an alkyl group having 2–4 carbon atoms; and M is an alkali metal cation, ½ an alkaline earth metal cation, or an ammonium ion having the formula

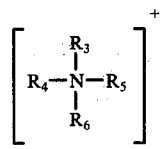

in which each of $R_3$, $R_4$, $R_5$, and $R_6$ is hydrogen, and alkyl group having 1–4 carbon atoms, or a hydroxyalkyl group having 1–4 carbon atoms;

b. a second acid having the formula

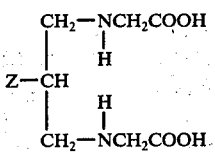

in which Z is H or OH; and c. a formaldehyde source selected from the group consisting of aqueous formaldehyde, trioxane, and paraformaldehyde, and maintaining the resulting mixture at a temperature (e.g., 50°–90° C (or 60°–85° C) effective for forming the first acid for a period of time (e.g., 4–24 hours (or 8–16 hours)) effective for forming the first acid, the phenol, the second acid, and the formaldehyde source being provided in amounts effective for forming the first acid and the inert solvent (inert reaction medium) being provided in an amount effective for dissolving the phenol. Preferred mole ratios of second acid to phenol to formaldehyde (as HCHO) are 1:2–8:2–4 (or 1:4:3).

The second acid can be fed into the system in which it will react to form the first acid as free second acid or as a salt having the formula

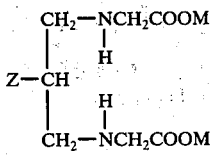

in which Z and M are as defined in Embodiment B. However, where feeding the second acid as said salt, the pH of the resulting mixture should be about 6 or lower (e.g., 2–6, or 1.5–5.9, or 3–6.5). Alternatively, providing the pH of the resulting mixture is about 6 or lower (e.g., 2–6, or 1.5–5.9, or 3–6.5), a salt having the formula

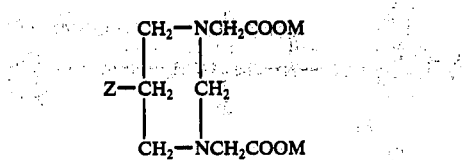

in which Z and M are as defined in Embodiment B can be used as a second acid source. Using either of these salts is fully equivalent to using the second acid per se.

Where feeding free second acid per se into the system the pH of the resulting mixture should be about 6 or lower (e.g., 2-6, or 1.5-5.9, or 3-6.5).

Preparation of such second acid is described in co-pending application Ser. No. 630,791, filed 11 Nov. 1975 which is now U.S. Pat. No. 3,988,367 assigned to W. R. Grace & Co.

The first acid can be recovered from the inert reaction medium (liquid reaction medium) in which it is formed (e.g., by centrifugation, filtration, or decantation). Alternatively, a chelate of the first acid with iron ions (or the like) can be formed in the liquid medium in which the first acid was prepared by reacting the first acid with a salt such as iron carbonate, iron sulfate, iron chloride, or the like, or with iron hydroxide. If desired, the chelate can be separated from the liquid medium (e.g., by centrifugation, filtration, or decantation).

Alternatively, the first acid can be converted to a salt (e.g., the sodium, potassium, calcium, or ammonium salt) by reacting the first acid (e.g., in the medium in which it (the first acid) was formed) with sodium carbonate, sodium hydrogen carbonate, sodium hydroxide, ammonia, potassium carbonate, calcium hydroxide, or the like. The thus formed salt of the first acid can be separated and recovered (e.g., by evaporation and/or centrifugation, filtration, or decantation). Alternatively, the salt while dissolved or suspended in the liquid medium can be reacted with an iron compound such as iron sulfate, iron chloride, iron nitrate, iron acetate, or the like, to form an iron chelate. If desired, the chelate can be separated from the liquid medium in which it was formed (e.g., by evaporation and/or centrifugation, filtration, or decantation).

More specifically, the first acid of Embodiment B can be converted to a salt having the formula

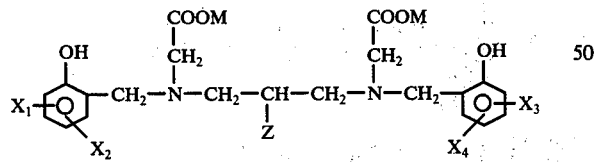

in which M, $X_1$, $X_2$, $X_3$, $X_4$, and Z are as defined in Embodiment B by treating said first acid, preferably in an aqueous medium with an amount of an alkali metal hydroxide or carbonate, or bicarbonate, or an alkaline earth metal hydroxide, or an ammonium hydroxide having the formula

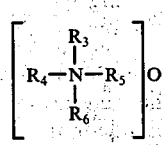

in which $R_3$, $R_4$, $R_5$, and $R_6$ are as defined in Embodiment B effective for bringing the pH of the system to about 8.5-10. At this pH all —$SO_3H$ groups (if any) present on the first acid and all —COOH groups present on the first acid will be converted to —$SO_3M$ groups and —COOM groups, respectively, but any phenolic —OH groups will remain as such (i.e., as phenolic —OH groups).

Where the pH is adjusted to about 2-5 with an alkali metal hydroxide or carbonate, or an alkaline earth hydroxide, or the ammonium hydroxide of Embodiment B, the —$SO_3H$ groups, if any, present on the first acid will be converted to —$SO_3M$ groups, but —COOH groups and phenolic —OH groups will remain unchanged (i.e., they will still be —COOH groups and phenolic —OH groups), respectively.

Where the pH is adjusted to about 12-14 with an alkali metal hydroxide, an alkaline earth hydroxide, or the ammonium hydroxide of Embodiment B, —$SO_3H$, —COOH, and phenolic —OH groups present on the first acid will be converted to —$SO_3M$ groups, —COOM groups, and phenolic —OM groups, respectively.

In other embodiments of the invention recited in Embodiment B:

1. The phenol is ⟨O⟩—OH and Z is H.

2. The phenol is ⟨O⟩—OH and Z is OH.

3. The phenol is (with OH and CH₃ substituents) and Z is H.

4. The phenol is (with OH and CH₃ substituents) and Z is OH.

5. The phenol is (with OH and CH₃ substituents) and Z is H.

6. The phenol is (with OH and CH₃ substituents) and Z is OH.

7. The phenol is (with OH and CH₃ substituents) and Z is H.

8. The phenol is (with OH and CH₃ substituents) and Z is OH.

9. The phenol is (with OH and OH substituents) and Z is H.

10. The phenol is (with OH and OH substituents) and Z is OH.

-continued

11. The phenol is 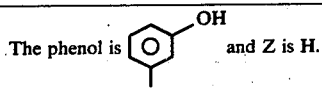 and Z is H.

12. The phenol is 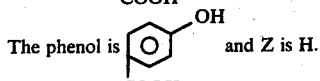 and Z is H.

13. The phenol is 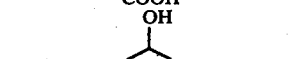 and Z is H.

14. The phenol is 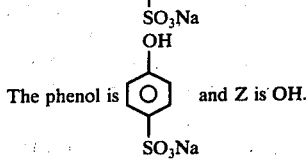 and Z is OH.

In the process of Embodiment B, where using a mixture of two phenols, one having the formula

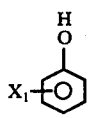

and the other having the formula

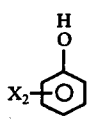

in which $X_1$, $X_2$, and Z are as defined in the above Summary with further condition that $X_1$ and $X_2$ are different, the product will be an admixture of three chelating compounds having the formulas:

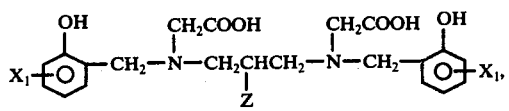

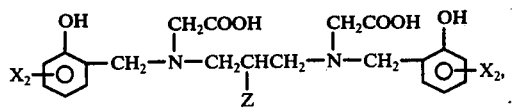
and

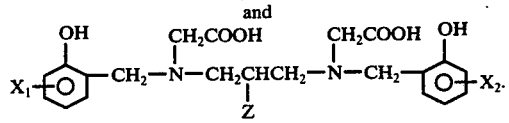

Likewise where using, in the process of Embodiment B, a mixture of two phenols having the formulas

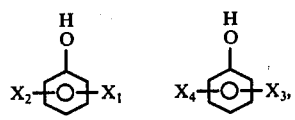

respectively, in which $X_1$, $X_2$, $X_3$, $X_4$, and Z are as defined in the above Summary — with the further condition that none of $X_1$, $X_2$, $X_3$, and $X_4$ are identical with each other — the product will be an admixture of three chelating compounds having the formulas:

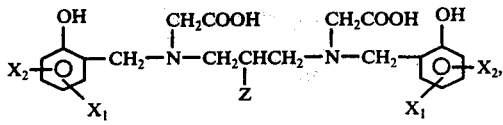

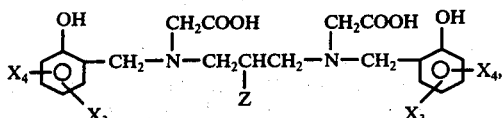
and

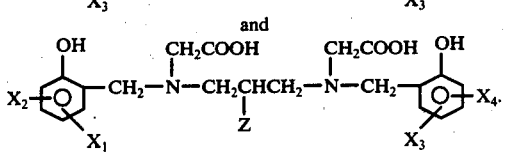

In such instance it is generally preferred (but not necessary) that the two phenols be mixed in about equimolar amounts.

In another preferred embodiment ("Embodiment C") this invention is directed to a process for preparing an acid having the formula

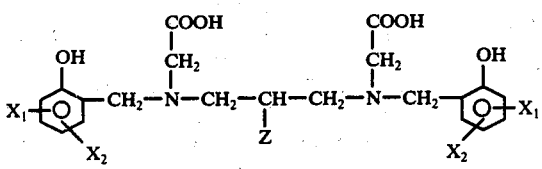

in which $X_1$, $X_2$, and Z are as defined in the above Summary, said process comprising: (a) forming a first mixture by admixing an aldehyde having the formula

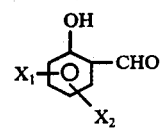

with methyl alcohol, ethyl alcohol, isopropyl alcohol, n-propyl alcohol toluene, benzene, or ethylene chloride (providing about 1.5-8.0 parts of solvent per part aldehyde); (b) forming a Schiff base having the formula

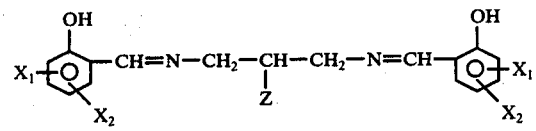

in which $X_1$, $X_2$, and Z are as defined in the above Summary, by admixing the first mixture and an amine having the formula

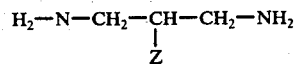

in which Z is defined in the above Summary to form a second mixture and heating the second mixture to its boiling temperature for one to three hours to cause refluxing and to remove by-product water by azeotropic distillation of the water; (c) separating the Schiff base from the mother liquor in which said base was formed; (d) reducing the Schiff base (e.g., with $NaBH_4$, LiAlH$_4$, H$_2$/Pd, or the like) to form a substituted amine having the formula

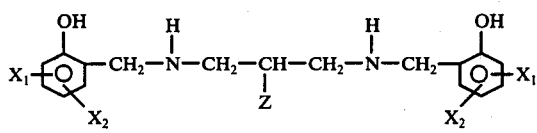

in which X$_1$, X$_2$, and Z are as defined in the Summary above; (3) forming a nitrile having the formula

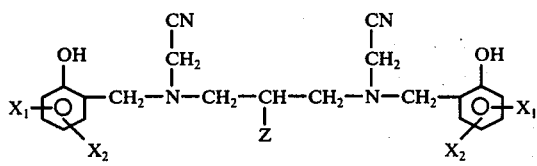

in which X$_1$, X$_2$, and Z are as defined in the above Summary, by admixing said substituted amine with glycolonitrile in a solvent such as methyl alcohol, ethyl alcohol, isopropyl alcohol, or a mixture of at least one of said alcohols with water (providing about 1.5 to 3.0 parts of alcohol per part of amine) to form a third mixture with glycolonitrile (preferably providing 1.9–2.1 moles of glycolonitrile per mole of amine), and separating the resulting nitrile from the mother liquor in which said nitrile was formed (alternatively, 1 mole of formaldehyde plus 1 mole of HCN can be used in place of each mole of glycolonitrile); (f) forming an acid hydrochloride having the formula

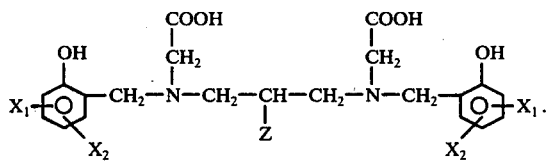

in which X$_1$, X$_2$, and Z are as defined in the above Summary by admixing said nitrile with hydrochloric acid (preferably concentrated hydrochloric acid, and preferably using about 5–20 moles of hydrochloric acid per mole of said nitrile) and maintaining the resulting mixture of hydrochloric acid and nitrile at about 50°–85° C for about four hours; and (g) converting the above-mentioned acid hydrochloride to the free acid by reacting said acid hydrochloride with a stoichiometric amount of sodium hydroxide (two moles per mole of the acid hydrochloride). Alternatively, a stoichiometric amount of another base (e.g., KOH, Ca(OH)$_2$, Ba(OH)$_2$, various ammonium hydroxides of the formula

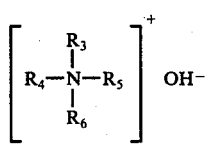

(in which R$_1$, R$_2$, R$_3$, and R$_4$ are defined in the above Summary), or the like) can be used in place of sodium hydroxide. A stoichiometric amount of KOH or

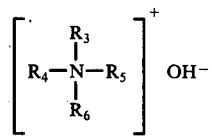

is two moles per mole of acid hydrochloride, and a stoichiometric amount of Ba(OH)$_2$ Ca(OH)$_2$ is one mole per mole of the acid hydrochloride.

The above-mentioned acid hydrochloride (or the corresponding free acid) can be converted to a salt by reacting it with an amount of a base (e.g., one of those listed above) effective for neutralizing the HCl moiety of the hydrochloride and for replacing the hydrogens of the —COOH groups with the cation of the base. If desired the hydrogens of the phenolic groups can also be replaced with the cation of such base.

Where the aldehyde in step (a) of Embodiment C is a mixture of two aldehydes, e.g.,

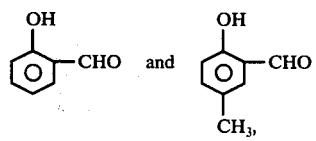

the final product (salt) will comprise three chelating compounds (chelating agents) having formulas:

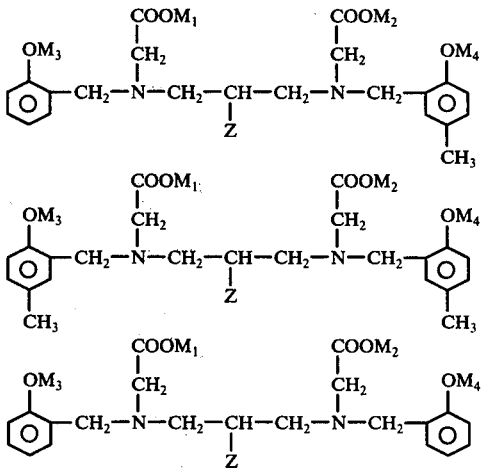

in which M$_1$, M$_2$, M$_3$, M$_4$, and Z are as defined in the above Summary.

Each of these three species (chelating agents) present in such instances can be identified (e.g., by gas chromotography, and the like) in the final product mixture without isolating the individual species from the final mixture.

Also, in such instances, the final product mixture can be used to prepare iron and other chelates of excellent quality — i.e., the chelates are prepared from the final product mixture without separating the individual species (the three chelating agents comprising the final product mixture). Such chelates of iron(III) and iron(II) ions (i.e., chelates of mixtures of three chelating agents formed by the above procedure from two aldehydes) can be used with excellent results to supply iron to citrus trees in calcareous soil.

The identity of Z is controlled by selecting the amine which is reacted with the aldehyde to form the desired Schiff base. Where the amine is 1,3-propanediamine, Z is H, and where the amine is 1,3-diamino-2-propanol, Z is OH.

The identity of $M_1$, $M_2$, $M_3$, and $M_4$ is controlled by the selection of the base or bases used to convert the above-mentioned acid hydrochloride to the free acid and a salt thereof. If the acid hydrochloride is treated with a stoichiometric amount of sodium (or potassium) hydroxide (2 moles of $OH^-$ per mole of acid hydrochloride) the H's of the carboxylic and phenolic groups will not be replaced by Na or K. If the acid hydrochloride (or the free acid) is treated with an amount of base (such as one of the bases listed above) effective for replacing the phenolic and carboxylic hydrogens with the cation of the base $M_1$, $M_2$, $M_3$, and $M_4$ will become identical with the cation of said base.

DETAILED DESCRIPTION OF THE INVENTION

The chelating agents of this invention are useful for chelating elements such as zinc, copper, cobalt, manganese, nickel, iron, and the like. This makes them (said chelating agents) useful additives for inclusion in metal plating baths.

The metal chelates of these compounds are useful for supplying trace elements to growing plants. The iron (iron(III) and iron(II)) chelates of these chelating agents are, as noted infra, especially useful for supplying iron to plants growing in calcareous soil.

As noted supra, this invention is also directed to the metal chelates of the chelating compounds recited in the above Summary and Preferred Embodiments. Said chelates are excellent materials for supplying trace elements (e.g., copper, manganese, cobalt) and iron to growing plants (e.g., beans, peas, soybeans, tomatoes, peppers, and the like) including plants growing in calcareous soil. These chelating agents form chelates which are useful for controlling the concentration of metallic ions in electroplating baths.

As stated supra, this invention is also directed to chelating compounds having the formulas recited in the above Summary and Preferred Embodiments, said compounds being excellent materials for chelating iron(II) and iron(III) compounds (including such iron compounds where present as "rust" stains on cloth, ceramic materials, porcelain and other surfaces, and the like, thereby to provide a convenient method for removing such stains).

In iron chlorosis (a plant malnutritional condition caused by iron deficiency) the area of a leaf between its veins is a marked yellow green in contrast to the dark green of the veins. In advanced iron deficiency, this contrast is lacking and instead the leaves have an ivory color, the plants become partially defoliated, and as a terminal result, die. Such iron deficiency can be caused by any of several factors. Some of these are: (1) an actual deficiency of iron in the soil; (2) high manganese and copper contents of the soil; and (3) an alkaline soil (pH above 7), which can be caused by a high soil content of calcium carbonate.

Although the value of EDTA (ethylenediaminetetraacetic acid) is recognized and utilized in agriculture and industry, the EDTA chelates of tri- and tetravalent metal ions are unstable in neutral and alkaline solutions, and these metal chelates hydrolyze in water to form insoluble metal hydroxides or hydrated metal oxides. The monosodium salt of the iron(III) EDTA chelate decomposes in aqueous solutions at pH 8 to iron(III) hydroxide and a soluble EDTA salt. This behavior imposes a serious limitation on the use of EDTA. The iron(III) EDTA chelate is effective in correcting iron deficiencies in plants grown in acid soils. However, in alkaline soils, this compound is economically ineffective in treating iron deficiency. Soil scientists have established that in alkaline soils iron(III) EDTA decomposes to liberate the iron as an insoluble iron(III) oxide or hydroxide in which form the metal ion cannot be absorbed by the root system of the plant and therefore is not available for plant nutrition. In order to overcome this defect of alkaline soils, the iron chelate of hydroxyethylethylenediaminetriacetic acid has also been recommended for plant nutrition, and although it is somewhat better than the EDTA chelate, it is economically ineffective for correcting iron chlorosis in calcareous soils.

A primary object of this invention is to provide iron chelates which are free of the aforedescribed deficiencies.

While the iron chelates of this invention can be applied to growing plants as an aqueous spray we prefer to apply these chelates to the soil.

In general, normal methods of applying micronutrients are followed with our iron chelate and other chelates. Our iron chelate (and our other chelates) can be mixed with water and applied as a liquid early in the growing season or applied to an absorbent earth which is subsequently applied to soil either with or without other fertilizers.

Excellent results can be obtained where applying the iron chelates at a rate to provide about 1 to 4 pounds of iron (reported as Fe) per acre. In certain instances lower or higher application rates may be desirable.

Because of our disclosure various other techniques for applying iron chelates to soil will be readily apparent to those skilled in the art.

A preferred technique for removing "rust" stains from a ceramic surface with the chelating compounds of out invention (e.g., the compounds disclosed in the above Summary) comprises allowing the rust covered surface to remain in contact with a solution of the chelating agent until the rust has been removed. It has been our experience that rust stains seem to differ greatly on their ease of removal. Presumably, this is related to the manner in which the stains were deposited or formed. It has been possible to remove rust stains simply by rubbing the stain with a 10% aqueous solution of the chelating agent on a rag or sponge. In other instances, it has been necessary to allow time for the chelating agent to act for a longer period. In these instances we can use several applications of a solution of the chelating agent or several "spongings" can be used. In most instances, heat accelerates the rust removal reaction.

A preferred technique for removing rust stains from cloth is to immerse the soiled cloth in an aqueous solution of our chelating agent (e.g., 0.25–10% by weight of our chelating agent) and allow the solution to remain in contact with the cloth until the stain is removed. This technique is excellent for removing rust stains from a soiled garment, a towel, or the like, but is too slow for use in textile manufacturing because cloth manufacturers prefer to use a fixed machine speed. In this instance, we prefer to add the chelating agent to a scouring both where said agent prevents the formation of rust stains on the cloth.

Because of our disclosure, various other techniques for removing rust stains with the compounds of our invention will be readily apparent to those skilled in the art.

The instant invention will be better understood by referring to the following specific but nonlimiting examples and procedures. It is understood that said invention is not limited by these examples and procedures which are offered merely as illustrations; it is also understood that modifications can be made without departing from the spirit and scope of the invention.

The examples were actually run.

The procedures, while not actually run, will illustrate certain embodiments of our invention.

EXAMPLE 1 a. 244.0 g (2.0 moles) of salicylaldehyde was dissolved in 400 ml MeOH. 74.1 g (1.0 mole) of 1,3-propanediamine in 100 ml of methanol was fed into the aldehyde over 1 hour from 20° C to reflux. After being stirred for 2½ hours, the reaction mixture was cooled to 10° C, and the bright yellow crystals of N,N'-disalicylidine-1,3-propanediamine (a Schiff's base) were filtered off. After drying in air, 277 g (98.2% yield) were obtained.

b. 70.5 g (0.25 mole) of the above Schiff's base was reduced by adding it portionwise to 10.1 g (0.26 mole) $NaBH_4$ suspended in 250 ml of isopropanol over 30 minutes from 22°–57° C. The slurry was held at 50°–58° C for 1½ hours. 150 ml of water was dripped in slowly with cooling, and the resultant thick mass was added to 2 l of water to precipitate the white amine. After stirring for a few minutes (ca. 10–15 minutes), the amine was filtered off, washed with water, and dried in air. 55.8 g (78% yield) of N,N'-di(o-hydroxybenzyl)-1,3-propanediamine was obtained. (Other replications of step (a) and this step (step (b)) were run to prepare about 5 moles of N,N'-di(o-hydroxybenzyl)-1,3-propanediamine.)

c. 1662.0 g (4.56 moles) of N,N'-di(o-hydroxybenzyl)-1,3-propanediamine was slurried in 6 l methanol at 50° C. 1,192 g (11.4 moles) of 54.4% glycolonitrile was added to the amine. Within 10 minutes the amine was dissolved. The solution was held at 40°–45° C for 1¼ hours. After cooling for 45 minutes to 36° C, the nitrile precipitated. The product was filtered off an hour later at 26° C and dried in air. 1,662.0 g (80% yield) of N,N'di(o-hydroxybenzyl)-1,3-propanediamine-N,N'-diacetonitrile was obtained.

d. All of the above nitrile (4.56 moles) was dissolved in 3 l (about 36 moles) concentrated HCl acid. The solution was allowed to stand 5 days at room temperature. Some $NH_4Cl$ and product hydrochlorides precipitated during this time. Then the reaction mixture was heated to 84° C over 2 hours. The mixture was cooled to room temperature over 2 hours, its volume was doubled with water, and its pH was adjusted to 4.0 with 50% NaOH solution. Cooling was used to keep the mixture below 50° C. During the neutralization, the product hydrochlorides precipitated and were sampled. After complete neutralization with NaOH solution the slurry was stirred overnight. The product acid was filtered off, reslurried in 6 l of water, filtered off, and dried in air. 636 g (34.6% yield) N,N'-di(o-hydroxybenzyl)-1,3-propanediamine-N,N'-diacetic acid (HBPD) was obtained. The HBPD was identified by elemental analysis, infrared spectroscopy, acid-base titration, and $Cu^{2+}$ titration.

EXAMPLE 2

13.2 g (0.069 mole) of 1,3-propanediamine-N,N'-diacetic acid (PDDA) was mixed with 36 g (0.38 mole) of phenol, 50 g of glacial acetic acid, and 50 ml of water. To this mixture 13.4 g (0.165 mole) of 37% formaldehyde dissolved in 125 ml of water was added with stirring. The pH was 2.6. The reaction mixture was left stirring unheated overnight. After two days standing at room temperature the mixture precipitated solid product. Two weeks later the reaction mixture was filtered to yield 13.0 g product, or 47% based on PDDA. After washing with acetic acid and acetone, the product produced a brilliantly redcolored iron chelate in highly alkaline solutions. A gas chromotogram showed that the product was (HBPD) — the same product obtained in Example 1, supra.

EXAMPLE 3

37.6 g (0.4 mole) of phenol in 25 ml of methanol was mixed with 19.0 g (0.1 mole) of PDDA and 13.7 g (0.2 mole) of 44% formaldehyde in 80 ml of $H_2O$. The mixture was heated 16 hours at 61° C. The product precipitated as white, fluffy solids. The solids were filtered off from the cooled reaction mixture, washed with methanol, and dried at 50° C. 17.0 g of 91.8% product was obtained, or 38.8% yield based on PDDA. The product was found to be HBPD as in Example 1 and had the same iron(III) chelating activity.

EXAMPLE 4

62.6 g (0.1 mole) of 39.3% disodium hexahydropyrimidine-1,3-diacetate ($HYPDANa_2$) solution was acidified to pH 3 with concentrated hydrochloric acid to give a solution of 19 g (0.1 mole) of PDDA, 3 g (0.1 mole) of formaldehyde, and sodium chloride. An additional 6.9 g (0.1 mole) of 44% formaldehyde was added to said solution. The whole mixture was diluted to 100 ml with water and added to 37.6 g (0.4 mole) of phenol in 30 ml of methanol. The mixture was reacted and the product was isolated in the same manner as in Example 3. 16.0 g of 91.8% HBPD was obtained. Thus the equivalence of neutralized $HYPDANa_2$ solutions and PDDA/formaldehyde solutions in the preparation of HBPD was shown.

EXAMPLE 5

The general procedure of Example 4 was repeated except that an additional 13.8 g (0.3 mole) of 44% formaldehyde was added instead of 6.9 g. The yield was 20.8 g.

EXAMPLE 6

The general procedure of Example 5 was repeated. However, in this instance the methanol was omitted. The product precipitated as a sticky mass of soft lumps. The product mass was mixed with MeOH to get product solids, which were filtered off and washed with water and methanol. 29.5 g of 92% HBPD was obtained after drying at 50° C or a 67.5% yield based on $HYPDANa_2$.

EXAMPLE 7

62.6 g (0.1 mole) of 39.3% $HYPDANa_2$ solution was acidified to pH 3.1–3.2 with about 18 ml of concentrated hydrochloric acid and 13.8 g (0.2 mole) of 44% formaldehyde was added. The resultant solution was mixed with 75.2 g (0.8 mole) of phenol and heated 16 hours at 70° C. The product was isolated as in Example 6. 36.8 g of 92.8% HBPD was obtained, or a 84.5% yield.

EXAMPLE 8

A sample of crude HBPD prepared by the general method of Example 3 was dissolved in aqueous sodium hydroxide to produce a solution having a pH of 8.8. The solution pH was adjusted with hydrochloric acid to 6.7, and the solution was extracted three times with ethyl ether. The aqueous layer was acidified with concentrated hydrochloric acid to pH 4.0 to precipitate the acid product. The precipitate was filtered off, washed with methanol and water, and dried. An infrared spectrogram and a gas chromatogram of the product was indentical to those of the product obtained in Example 1. A copper(II) chloride titration of the product at pH 9 indicated a molecular weight of 402.3 vs. 402 theoretical. These data along with a C, H, N, and O analysis established that the product was pure HBPD. The impurity in 90-92% methanol washed HBPD products obtained from the reaction mixtures was found to be mostly phenol, which HBPD complexes strongly.

EXAMPLE 9

The procedure of Example 7 was repeated to prepare HBPD. However, 50% sodium hydroxide was added to the whole reaction mixture to raise the pH to 8 and dissolve the product mass. The aqueous mixture was extracted with two 100 ml portions of ethyl ether and acidified with hydrochloric acid to pH 4 to precipitate the acid product. The product was slurried in water and then in methanol for washing. 34.7 g of dried pure HBPD, or an 86.3% yield was obtained.

Various other solvents were found useful for extracting the reaction mixture as in Example 9. Among them are isopropyl and butyl ether; ethyl, n-butyl, and n-amyl acetate; n-hexyl, n-amyl, i-amyl, and t-amyl alcohol; and ethyl and methyl isobutyl ketones.

EXAMPLE 10

A reaction mixture was prepared by admixing 62.6 g of an aqueous system consisting essentially of water and $HYPDANa_2$ and analyzing 39.3% $HYPDANa_2$ (0.1 mole of $HYPDANa_2$), 13.8 g of an aqueous formaldehyde solution analyzing 44% HCHO (0.2 mole HCHO) and 41.8 g of an aqueous system consisting essentially of phenol and water and analyzing 90% phenol (0.4 mole phenol). The pH of the reaction mixture was about 3. The reaction mixture was maintained at 70° C for 16 hours and then cooled to about 25° C. The pH of the cooled reaction mixture was raised to 8 and the resultant solution was extracted with three 100 ml portions of ethyl ether. The aqueous layer was analyzed for HBPD by spectrophotometry (at 490 nm) of the solution after converting the HBPD product to its iron(III) chelate. The yield in solution was 84.3% based on $HYPDANa_2$ charged. In a similar run with a reaction time of eight hours the yield was 77.7%.

EXAMPLE 11

75.8 g (0.1 mole) of 34.6% disodium 5-hydroxyhexahydropyrimidine-1,3-diacetate was neutralized with hydrochloric acid to about pH 3 to give a solution of 20.6 g (0.1 mole) of 1,3-diamino-2-propanol-N,N'diacetic acid, 3 g (0.1 mole) of formaldehyde, and sodium chloride. 13.8 g (0.2 mole) of 44% formaldehyde was added to the solution. The resultant mixture was reacted with 37.6 g (0.4 mole) of phenol in 35 ml of MeOH at 60° C for 16 hours. A thick white product slurry was obtained. The product was filtered off, slurried in MeOH, filtered, washed, and dried at 50° C. 13.2 g (32.5% yield) of N,N'-di(o-hydroxybenzyl)-1,3-diamino-2-propanol-N,N'-diacetic acid (HBPD-OL) was obtained.

EXAMPLE 12

43.2 g (0.4 mole) of m-cresol, 20.7 g (0.3 mole) of 44% $CH_2O$, and 62.6 g (0.1 mole) of $HYPDANa_2$ (neutralized to pH 3) in 150 ml of a 33% aqueous methanol solution was allowed to stand at room temperature for 15 days. The product that precipitated contained 8% m-cresol after washing. Isolation of the product as in Example 11 yielded 32.0 g, or 74% yield, of white N,N'-di(2-hydroxy-4-methylbenzyl)-1,3-propanediamine-N,N'-diacetic acid.

EXAMPLE 13

55.6 g (0.4 mole) of p-nitrophenol was substituted for m-cresol in the general procedure of Example 12. 15 g of beige crystals were isolated. The product was identified as N,N'-di(2-hydroxy-5-nitrobenzyl)-1,3-propanediamine-N,N'-diacetic acid.

EXAMPLE 14

43.2 g (0.4 mole) of o-cresol was substituted for m-cresol in the general procedure of Example 12. 20 g of N,N'-di-(2-hydroxy-3-methylbenzyl)-1,3-propanediamine-N,N'-diacetic acid was isolated.

EXAMPLE 15

44.0 g (0.4 mole) of resorcinol was substituted for m-cresol in the general procedure of Example 12. The reaction mixture produced a deep purple iron chelate where admixed with iron(III) chloride in a strongly alkaline solution.

EXAMPLE 16

44.0 g (0.4 mole) of salicylic acid was substituted for m-cresol in the general procedure of Example 12. The reaction mixture produced an orange iron chelate where admixed with iron(III) chloride in a strongly alkaline solution.

EXAMPLE 17

3,439 g of technical HBPD analyzing 90% HBPD (i.e., 7.7 moles of HBPD) was dissolved with 50% NaOH and an amount of water to produce about 5 gallons of a solution having a pH of 10. 3,210 g (7.7 moles) of 39% $FeCl_3$ was added concurrently with additional 50% NaOH over one hour. A total of about 30 moles of 50% NaOH was added. The final pH of the mixture was 8.2. After being stirred overnight, the mixture was concentrated by boiling to a thick slurry of about 4 gallons. 4 one-liter portions were filtered and each residue was washed with 200 ml of water, air dried, and weighed. Recovery was 93% of theory. Analysis of the brick red product (HBPDNaFe, the iron(III) chelate of the mono sodium salt of HBPD) by visible spectrophotometry at 490 nm showed an active ingredient (said iron chelate) content of 99.6%.

EXAMPLE 18

HBPD was prepared as in Example 7. The total reaction mixture was diluted with 150 ml of water, the pH of the mixture was raised to 8.38 with 50% NaOH, and the resultant solution was extracted with three 100 ml portions of ethyl ether. To the aqueous layer was added 36.0 g (0.086 mole) of 39% $FeCl_3$ concurrently with 50% NaOH so that the final pH was 8.3. The mixture was boiled 3 hours to reduce the volume to about 200 ml. The iron chelate was filtered off, washed with 50 ml of water, and dried at 60° C. 41.2 g, a 79.5% yield based on PDDA, of HBPDNaFe was obtained. Spectrophotometric analysis showed a 92% active ingredient, and a chloride titration indicated 2.5% NaCl.

EXAMPLE 19

20.1 g (0.05 mole) of HBPD was dissolved in 300 ml of water containing 9 ml of concentrated hydrochloric acid (ca. 0.1 mole). The temperature of the solution was brought to 73° C and 3.0 g (0.05 mole) of sponge iron was added. The mixture was stirred 8 hours 80° C. During this time hydrogen evolved smoothly as $HBPDFeH_2.2$ HCl formed, but slowed down. Another 3.0 g (0.05 mole) of sponge Fe was added and heating was continued another 2 hours. The excess iron was filtered off and washed. 12.0 g (0.15 mole) of 50% NaOH was added to the colorless filtrate to give initially a white precipitate of $HBPDFeH_2$ (the iron(II) chelate of the acid form of HBPD having two acidic hydrogens per molecule), which dissolved to give a colorless solution of HBPDFeNaH (the iron(II) chelate of a sodium salt of HBPD having one acidic hydrogen per molecule), which quickly oxidized to HBPDFeNa. Analysis of the oxidized solution by spectrophotometry showed a 66.2% yield of ferrous chelate, with 26% of the HBPD remaining unreacted.

EXAMPLE 20

0.4 lb. of HBPDNaFe per tree was applied to the soil beneath iron chlorotic orange trees growing in calcareous soil (pH 8.0) in central Florida. Within 5 weeks, greening of the yellow chlorotic leaves was noted. After 15 weeks, one of the trees was visually examined and rated. 82% of the marked chlorotic twigs had greened, and only about 10% of all of the tree's leaves appeared chlorotic. Such performance represents a commercially satisfactory degree of effectiveness for citrus trees growing in a calcareous soil of pH 8.0 and is comparable to the performance of Chel 138 (a commercially available iron chelate effective for use in calcareous soil).

PROCEDURE 1

The procedure of Example 12 can be used to prepare other ring-substituted HBPD chelating agents by replacing m-cresol with an equivalent amount of a phenol such as p-N,N-dimethylaminophenol, sodium p-phenolsulfonate, p-hydroxybenzoic acid, p-cyanophenol, 2,4-dimethylphenol or the like. Analogous ring-substituted N,N'-di(o-hydroxybenzyl)-1,3-diamino-2-propanol-N,N'-diacetic acids can be prepared by using 1,3-diamino-2-propanol-N,N'-diacetic acid instead of PDDA.

PROCEDURE 2

The use of only 3 moles of NaOH per mole of HBPD during the preparation of ferric chelate by the general procedure of Example 17 will yield a purple precipitate of HBPDFeH (the iron(III) chelate of HBPD).

PROCEDURE 3

20.1 g (0.05 mole) of HBPD can be slurried in 300 ml of water and 13.9 g (0.05 mole) of $FeSO_4.7\ H_2O$ can be added thereto. The HBPD will dissolve to yield colorless solution of $HBPDFeH_2.H_2SO_4$. The addition of 8.0 g (0.1 mole) of 50% NaOH under nitrogen will produce a white precipitate of $HBPDFeH_2$ (the iron(II) chelate of HBPD). The addition of another 8.0 g (0.1 mole) of 50% NaOH under nitrogen will yield a colorless solution of $HBPDFeNa_2$. Removal of the nitrogen blanket will allow the rapid oxidation of the ferrous chelate to the deep wine-red ferric chelate, HBPDFeNa.

PROCEDURE 4

One mole of HBPD.2 HCl, precipitated and recovered from the hydrolysis mixture of Example 1, for example, can be reacted with about 3 moles (excess) of powdered iron, one mole of $FeCO_3$, one equivalent of an iron oxide (such as $Fe_2O_3$ and $Fe_3O_4$), or one equivalent of iron hydroxide and three moles of NaOH to produce HBPDFeNa. (One equivalent of an iron compound is an amount of that compound that will provide one mole of iron reported as Fe.)

PROCEDURE 5

Chelating compounds having the formula

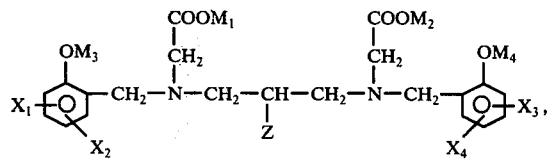

in which $M_1$, $M_2$, $M_3$, $M_4$, Z, $X_1$, $X_2$, $X_3$, and $X_4$ are as defined in the above Summary, can be converted to iron chelates using the general method of Examples 17, 18, or 19. Any of the resulting iron chelates can be applied to soil including calcareous soil in which chlorotic plants (e.g., citrus trees) are growing by using the general method of Example 20 or by spraying an aqueous solution of the iron chelate on the chlorotic plant (e.g., on the leaves of a chlorotic tree). In each instance such application of iron chelate will produce a very marked decrease in the chlorosis of the treated plants.

PROCEDURE 6

Chelating compounds having the formula

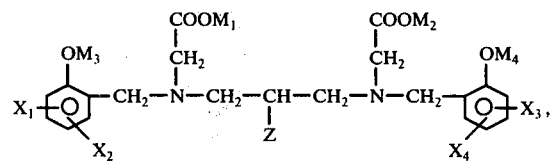

in which $M_1$, $M_2$, $M_3$, $M_4$, Z, $X_1$, $X_2$, $X_3$, and $X_4$ are as defined in the above Summary, can be used to remove iron rust stains from cloth, glass surfaces, plastic surfaces, tile surfaces, ceramic surfaces, metal surfaces, dishes, and the like. This (the removal of iron rusts stains) can be accomplished by placing an aqueous solution or dispersion of the chelating compound in contact with the rust stain and allowing the chelating compound to chelate the iron rust which can then be removed (e.g., by sponging with a damp cloth or sponge or by flushing with a stream of water). In the case of a rust stained cloth, such cloth can be soaked in an aqueous solution (or dispersion) of the chelating compound to chelate the iron rust, and the resulting chelated iron can be washed from the cloth.

In some instances more than one treatment will be required to remove an iron rust stain from a cloth or surface.

PROCEDURE 7

A product amine having the formula

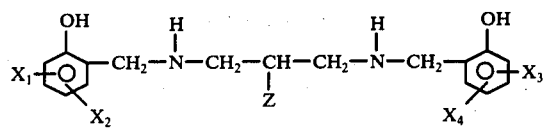

in which Z is —H or —OH and each of $X_1$, $X_2$, $X_3$, and $X_4$ is of hydrogen, —OH, an alkyl group having 1–4 carbon atoms, —CN, —SO$_3$M, or —COOM in which M is a hydrogen ion, an alkali metal ion, one-half an alkaline earth metal ion, or an ammonium ion having the formula

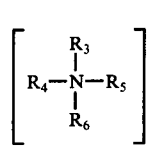

in which each of $R_3$, $R_4$, $R_5$, and $R_6$ is hydrogen, an alkyl group having 1–4 carbon atoms, a hydroxyalkyl group having 1–4 carbon atoms, or an alkyl group having 1–4 carbon atoms can be prepared by using the general method of the first two paragraphs of Example 1 wherein the method is modified by replacing the salicylaldehyde with aldehyde(s) having the formula(s)

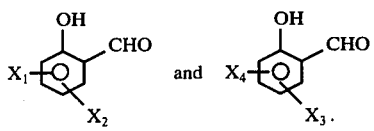

If it is desired to have $X_1$ and $X_2$ identical with $X_3$ and $X_4$, respectively, only one aldehyde is used, otherwise two aldehydes are used.

In such method: (a) the use of 1,3-propanediamine (as in Example 1) will produce a product amine in which Z is —H; and (b) the use of 1,3-diamino-2-propanol rather than 1,3-propanediamine will produce a product amine in which Z is —OH.

Where using two aldehydes, a mixture of three product amines will be obtained, to wit:

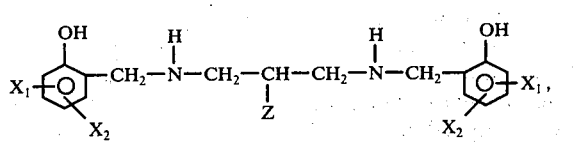

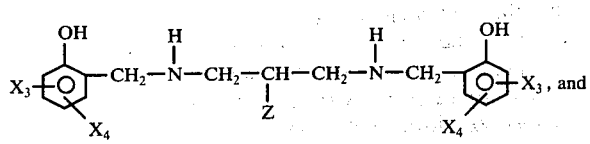

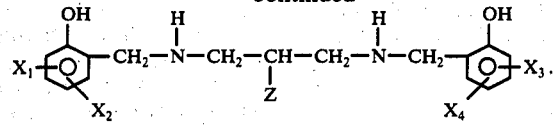

As used herein the term "a hydroxyalkyl group having 1–4 carbon atoms" means a group such as:
(a) —CH$_2$OH; (b) —CH$_2$CH$_2$OH;

(d) —CH$_2$CH$_2$CH$_2$OH;

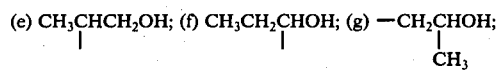

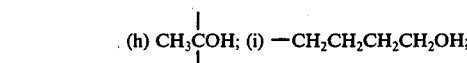

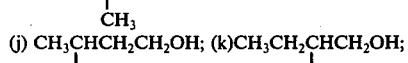

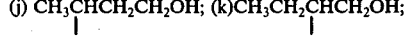

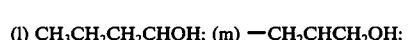

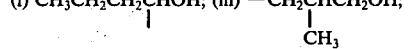

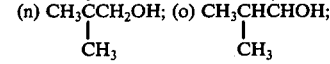

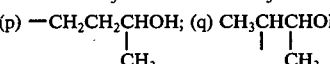

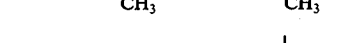

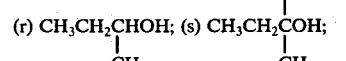

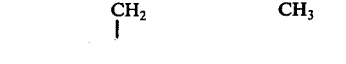

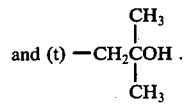

As used herein the term "mole" has its generally accepted meaning — i.e., a mole of a substance is the quantity of the substance having the same number of molecules of the substance as there are atoms of carbon in 12 g of pure $^{12}$C.

As used herein the term "g" means gram or grams.

As used herein the term "HBPD" means N,N'-di(o-hydroxybenzyl)-1,3-propanediamine-N,N'diacetic acid.

As used herein the term "HYPDANa$_2$" means disodium hexahydropyrimidine-1,3-diacetate.

As used herein the term "PDDA" means 1,3-propanediamine-N,N'-diacetic acid.

As used herein the term "PDDA-OH" means 1,3-diamino-2-propanol-N,N'-diacetic acid.

As used herein "HBPDNaFe" or HBPDFeNa" means the iron(III) chelate of the sodium salt of HBPD.

As used herein "HBPDFe$_2$H$_2$" means the iron(II) chelate of the acid form of HBPD.

As used herein "HBPDFeNaH" means the iron(II) chelate of the monosodium salt of HBPD.

As used herein the term "HBPDFeH" means the iron(III) chelate of HBPD.

As used herein the term "HBPD-OL" means N,N'-di(o-hydroxybenzyl)-1,3-diamino-2-propanol-N,N'-diacetic acid.

As used herein the term "CH₂O" means formaldehyde.

As used herein the term "nm" means nanometer(s).

As used herein "l" means liter(s).

As used herein "MeOH" means methyl alcohol.

We claim:

1. A compound having the formula

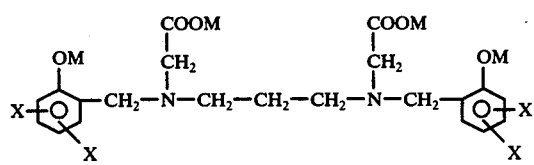

in which:

a. each X is a member selected from a first group consisting of (i) hydrogen; (ii) an alkyl group having 1-4 carbon atoms; (iii) —SO₃M; and (iv) —COOM;

b. M is a member selected from a second group consisting of (i) a hydrogen ion; (ii) an alkali metal ion; (iii) one-half an alkaline earth metal ion; and (iv) an ammonium ion having the formula

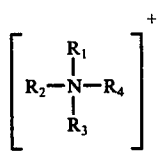

in which each of R₁, R₂, R₃, and R₄ is a member selected from a third group consisting of (A) hydrogen; (B) an alkyl group having 1-4 carbon atoms; and (C) a hydroxyalkyl group having 1-4 carbon atoms.

2. The compound of claim 1 in which M is a hydrogen ion or a sodium ion.

3. A compound having the formula

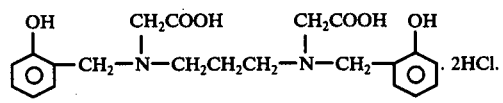

4. A compound having the formula

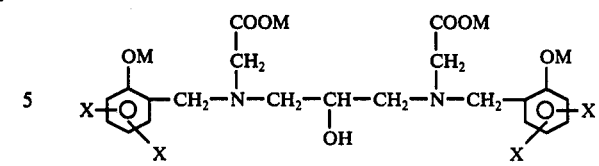

in which:

a. each X is a member selected from a first group consisting of (i) hydrogen; (ii) an alkyl group having 1-4 carbon atoms; (iii) —SO₃M; and (iv) —COOM;

b. M is a member selected from a second group consisting of (i) a hydrogen ion; (ii) an alkali metal ion; and (iii) one-half an alkaline earth metal ion; and (iv) an ammonium ion having the formula

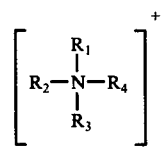

in which each of R₁, R₂, R₃, and R₄ is a member selected from a third group consisting of (A) hydrogen; (B) an alkyl group having 1-4 carbon atoms; and (C) a hydroxyalkyl group having 1-4 carbon atoms.

5. The compound of claim 4 in which M is a hydrogen ion or a sodium ion.

6. A compound having the formula

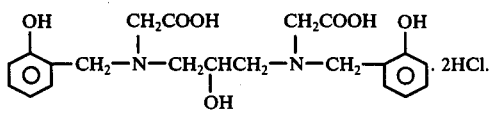

7. A compound having the formula

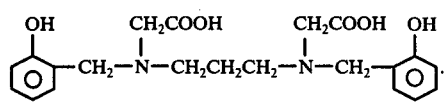

8. A compound having the formula

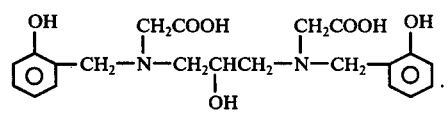

* * * * *